(12) United States Patent  
Jackson

(10) Patent No.: US 9,233,027 B1  
(45) Date of Patent: Jan. 12, 2016

(54) EARSCRUBBER

(71) Applicant: Joel Jackson, Sherman Oaks, CA (US)

(72) Inventor: Joel Jackson, Sherman Oaks, CA (US)

(73) Assignee: Karewell Brands, Inc, Sherman Oaks, CA (US)

(*) Notice: Subject to any disclaimer, the term of this patent is extended or adjusted under 35 U.S.C. 154(b) by 0 days.

(21) Appl. No.: 14/545,763

(22) Filed: Jun. 16, 2015

Related U.S. Application Data

(63) Continuation-in-part of application No. 14/535,450, filed on Nov. 7, 2014.

(51) Int. Cl.
    *A61F 9/00*     (2006.01)
    *A61F 11/00*     (2006.01)

(52) U.S. Cl.
    CPC .............. *A61F 11/006* (2013.01); *A61F 11/00* (2013.01)

(58) Field of Classification Search
    CPC ........ A61F 11/006; A61F 13/38; A61F 11/00
    USPC .............................. 606/159, 160, 162; 604/1
    See application file for complete search history.

(56) References Cited

U.S. PATENT DOCUMENTS

2008/0300527 A1* 12/2008 Bivins .................. A61F 11/006  
    604/1

FOREIGN PATENT DOCUMENTS

| AU | 2013100584 | | 8/2013 |
| EP | 0158543 | A1 * | 10/1985 |
| EP | 0875221 | | 11/1998 |
| WO | 96/37172 | | 11/1996 |

OTHER PUBLICATIONS

Machine translation of EP 0158543 (Collin). Published Oct. 1985.*

* cited by examiner

*Primary Examiner* — Katherine M Shi

(57) ABSTRACT

A disposable plastic device insertable into an ear canal that is used to scrape wax and debris from the ear canal without injuring the ear canal and ear drum when rotated inside the ear canal. The device is constructed using an elongated shaft which is adapted to be grasped and rotated. Accordingly, the preferred embodiment consists of a first plurality of blades attached to the first end of the elongated shaft having a curved concave clockwise shape. And a second plurality of blades attached to the second end of the elongated shaft having a curved convex clockwise shape in the opposite direction. The device has a dome tip at the shaft first end and the shaft second end that are tapered from the shaft first tip and shaft second tip respectively, to the midpoint of the blades.

7 Claims, 4 Drawing Sheets

EARSCRUBBER

CROSS-REFERENCE TO RELATED APPLICATIONS

This application is a Continuation in Part Application and claims the benefits of the U.S. Utility application Ser. No. [14/535,450] filed [Nov. 7, 2014] by the present inventor. This US Utility Application is incorporated herein by reference.

BACKGROUND OF INVENTION

There exists many patent documents and commercial products designed to clean the wax from the ear canal without damaging or irritating the ear canal. The most common is the cotton swab, referred to generically (and incorrectly) as a Q-tip. The cotton swab consists of a small wad of cotton wrapped around one or both ends of a short rod or shaft, usually made of either wood, rolled paper, or plastic. However use of the cotton swab is the most common cause of eardrum punctures, and not recommended due to the limitations of the design at removing wax and debris.

The cotton swab works well to remove water and some particulates from the ear canal but is limited in its design at removing earwax and debris. The smooth tip of the cotton swab cannot suck, scrape, or cut earwax and debris from the ear canal, instead it smears and pushes wax deeper inside the ear canal without removing the wax from the surface of the ear canal. Lastly, cotton swabs can result in injury to the ear drum due to the need to press and dig inside the ear canal in an attempt order to gather earwax and debris from the ear canal.

Sittler EP 0875221 describes a device insertable into an ear canal that is used to scrape wax and debris from the ear canal without injuring the ear canal and ear drum when rotated inside the ear canal. The device composes of a shaft with a bulbous shape at both tips of the shaft, and a plurality of blades or strands that extend axially out from the shaft in same axial direction of the shaft. The blades are used to scrape the wax from the ear canal when rotated inside the ear canal. The device is manufactured in several steps. The first step involves injection molding the shaft and injection molding the strands. The next step involves joining the strands to the blade by welding them and shaping them to the bulbous ends, then cutting the excess material from the tips of the strands. This process involves several steps and requires expensive equipment in addition to the injection mold. The automation of such a process is not easy and results in a tooling cost, staff and relatively high maintenance. Moreover because of the sequence of steps involved, the manufacturing time unit is relatively long, which further increases the manufacturing cost and the cost to the consumer.

Serra WO 96/37172 describes a device insertable into an ear canal that is used to scrape wax and debris from the ear canal without injuring the ear canal and ear drum when rotated inside the ear canal. The device composes of an elongated shaft and a plurality of blades or strands that extend axially out from the shaft in same axial direction of the shaft. The distal ends of the tips of the device have various shapes including an ovoid and rounded shapes. One problem with Serra device is that Serra teaches a device that comprises of a rounded and or ovoid shaped tip that may push wax deeper into the ear canal. Since a rounded tip is flat at its axis, it will push wax further inside the ear canal causing wax impactation. Oval shaped tips can damage the ear drum if they are too acute. Furthermore, Serra discloses a device with helical and parallel blade orientations. Since the ear canal is a tubular shape, cut geometry teaches that the entire surface of a blade must intersect to the surface of the ear canal at an angle ranging from 0 to 45 degrees to scrape and cut an optimal amount of earwax and debris from the surface of the ear canal. While I believe an optimal amount of earwax and debris is scraped and cut from the surface of the ear canal when the entire blade intersects the entire surface of the ear canal, I don't wish to be bound by this. Nonperpendicular orientations therefore do not scrape or cut an optimal amount of earwax and debris from the surface of the ear canal since the entire surface of the blade does not intersect the surface of the ear canal. Although Serra proposes a parallel blade orientation, a parallel blade orientation does not remove an optimal amount of earwax and debris from the ear canal since there no curvature mechanism to gather the earwax and debris as it is scraped from the surface of the ear canal so earwax and debris escapes from the tips of the blades as the device is rotated inside the ear canal.

Coe AU 2013100584 describes another orientation of a device insertable into an ear canal that is used to scrape wax and debris from the ear canal without injuring the ear canal and ear drum when rotated inside the ear canal. The device composes of an elongated shaft and four blades that are extended orthogonally from the shaft. The orientation of the blades are described as crosses with a lip-like projection forming the end of the blades. In other words, when viewed from a cross-sectional viewpoint, the blades appear like four straight perpendicular intersecting lines with a curve at the distal ends of each of the four straight lines. One limitation to Coes device is that blades that do not curve from the base of the shaft which will require the user to use greater rotational force due to friction generated by the earwax and debris as it impacts the wall of the straight stem orientation of the blades. Further, Coe does not disclose the arc radian of the lip-like projections extending from the tips of the blades. If the lip-like projections are too obtuse, greater than 50 degrees, earwax and debris will escape the edges of the lip-like projections when the device is rotated inside the ear canal and therefore will not be gathered by blades. If the lip-like projections are too acute, less than 20 degrees, earwax and debris will be pushed longitudinally inside the ear canal by the outer surface of the lip-like projections and therefore will not gather the earwax and debris. Further, if the lip-like projections are too acute, the edges of the lip-like projections will not scrape, cut and gather an optimal amount of earwax and debris from surface of the ear canal because the edges of the blades will be at a negative degree or angle to the surface of the ear canal and therefore earwax and debris will glide over the outer surface of the blade as it is rotated inside the ear canal. Furthermore, Coe does not discuss the criticality of the edges of the blades to the outcome of cutting and scraping earwax and debris from surface of the ear canal. If the edges of the blades are too obtuse, greater than 7 degrees the edges will be too obtuse and will require greater rotational force to cut through the earwax and debris because friction will generate between the obtuse edge and the earwax and debris.

OBJECTS AND ADVANTAGES

The preferred embodiment herein solves the problem of providing a disposable device for cleaning the ear canal safely, while being manufactured inexpensively and using a single manufacturing step. The preferred embodiment and cut, scrapes and gathers an optimal or maximum amount (compared to similar rotational devices) of earwax and debris from the ear canal while requiring the user to use the least amount of rotational force by the user when the device is rotated inside the ear canal.

The preferred embodiment is a disposable device insertable into an ear canal that is used to scrape wax and debris from the ear canal without injuring the ear canal and ear drum when rotated inside the ear canal. The device is constructed using a dually tapered elongated shaft having a circular section which is adapted to be grasped and rotated. The shaft is dually tapered as the distance from the shaft circular section is increased, with the shaft first end and shaft second end and ending the taper by having a regular cylindrical shape.

Accordingly, the preferred embodiment consist of a first plurality of blades attached to the first end of an elongated shaft having a curved concave clockwise shape occurring in the first curvature direction. A second plurality of blades attached to the second end of an elongated shaft having a curved convex clockwise shape in the second curvature direction. A first plurality of blades are uniformly radially spaced about the end of the longitudinal axis of the shaft being connected to the shaft parallel to the longitudinal axis adapted to cut and scrape an optimal amount of earwax and debris from the surface of the ear canal. The second plurality of blades are uniformly radially spaced about the opposite end of the longitudinal axis of the shaft being connected to the shaft parallel to the longitudinal axis adapted to cut and scrape optimal amount of earwax and debris from the surface of the ear canal. A first plurality of blades connected to a shaft having a first space between adjacent blades adapted to collect and store earwax and debris. The second plurality of blades connected to a shaft having a second space between adjacent blades adapted to collect and store earwax and debris. A first plurality of blades curved from the base of the shaft at adapted to required less rotational force when rotated inside the ear canal. The second plurality of blades curved from the base of the opposite end of the shaft adapted to required less rotational force when rotated inside the ear canal. A first plurality of blades having first arc radian ranging from 20 degrees to 50 degrees adapted to cut and scrape the surface of the ear canal at a radius ranging from 0 degrees to 45 degrees. The second plurality of blades having a second arc radian ranging from 20 degrees to 50 degrees adapted to cut and scrape the surface of the ear canal at a radius ranging from 0 degrees to 45 degrees. A first plurality of blade edges having a first acute edge angle ranging from 3 to 7 degrees adapted to cut through earwax and debris with less rotational force. The second plurality of blade edges having a second acute edge angle ranging from 3 to 7 degrees adapted to cut through earwax and debris with less rotational force.

The preferred embodiment has a dome tip at the first and second end of the axis of blades which is adapted to protect the ear canal from sharp edges that can result during injection molding such as not in the case of the prior art. At the first and second end of the shaft, the device has a bevel shape at the shaft first end that tapers from the first shaft tip to the midpoint of the blades which is adapted to minimize the amount of earwax and debris that is pushed inside the ear canal upon insertion. The device has a bevel shape at the shaft second end that tapers from the second shaft tip to the midpoint of the blades which is adapted to minimize the amount of earwax and debris that is pushed inside the ear canal upon insertion. As the bevel end is inserted, it penetrates the earwax and debris as opposed to pushing it further inside the ear. Further the bevel shaped tip is specially adapted to collect earwax and debris located deeper inside the ear canal due to the ability of its shape to be inserted further inside the ear canal as opposed to other tip orientations which is a significant distinction over the prior art.

The preferred embodiment is made from plastic consisting of but not limited to polypropylene and polyethylene. Specification of plastic material is critical to the ability of the device to be able to both be manufactured in the most economical way with respect to both procurement cost and the ability of the device to be injection molded in a single step. 3D printing methods can achieve the production of the preferred embodiment but not at a reasonable cost to the consumer so the preferred method of production is to use injection molding methods. The procurement cost of the plastic material otherwise known as resin, must be inexpensive so that the cost to the consumer will be inexpensive.

The preferred embodiment overcomes the injection molding challenges of manufacturing the device in a single injection molding step out of hard plastic with undercuts inherent in the design of the device. An undercut in shape of the device in other words any indentation or protrusion in the shape of the device will prevent the device from being directly ejected from an injection molding machine. Thus, the device will be difficult to manufacture in a single injection molding step as in the case of the prior art. The curvatures of the blades in the preferred embodiment are designed with undercuts which make the device difficult to injection mold in a single step. If the device contains one or more undercuts and is injection molded using a soft plastic otherwise referred to as a plastic with a low shore value, the undercut can be overcome and removed from the injection mold in a single step however soft plastic material may not be as effective in cutting and gathering earwax and debris as it will require greater rotational force from the user to gather earwax and debris. If the device contains one or more undercuts and is manufactured from a hard plastic otherwise referred to as a plastic a high shore value, the undercut cannot be easily injection molded in a single step but may be more effective in cutting and gathering earwax and debris thus requiring less rotational force from the user.

Furthermore, the present invention is manufactured using an inexpensive and high shore value plastic consisting of but not limited to polypropylene and polyethylene. The device is therefore difficult to injection mold in a single step because a separate component called a slider has to be specially designed and inserted into the injection mold in order for the entire device to be ejected from the injection mold in a single step, a significant difference over the prior art.

NUMERALS

Figure 1:
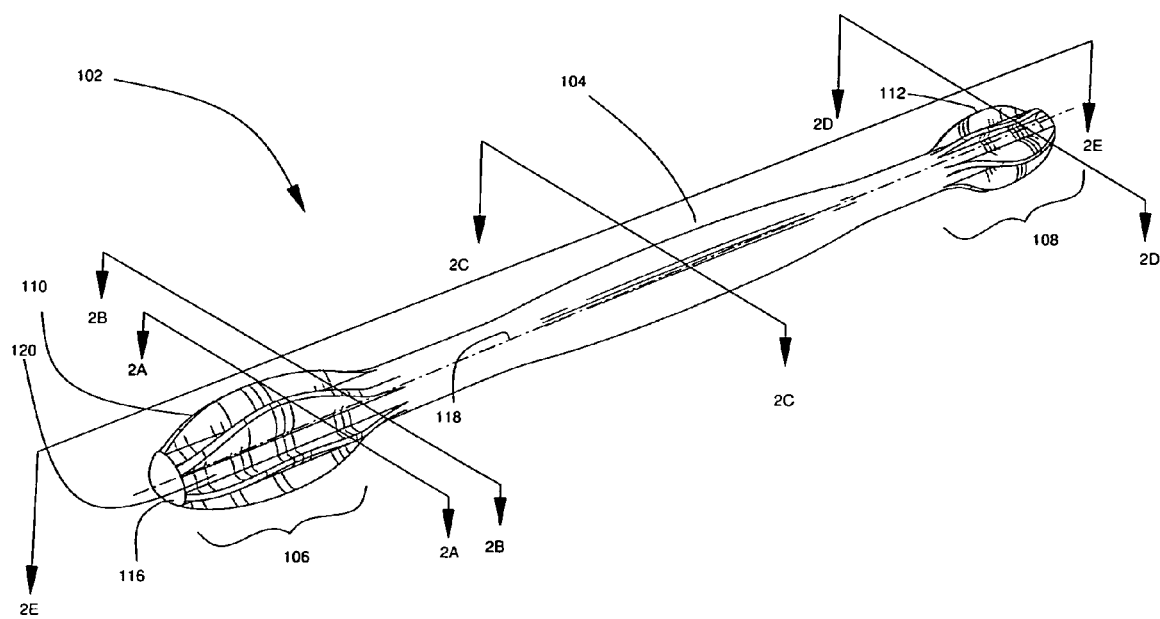
FIG. 1 is a perspective view of the first embodiment of the current invention.
Figure 2A:
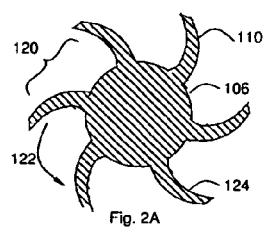
FIGS. 2A, 2B, 2C, and 2D are four sectional views of FIG. 1, the sections taken perpendicular to the longitudinal axis of the first embodiment.
Figure 3:
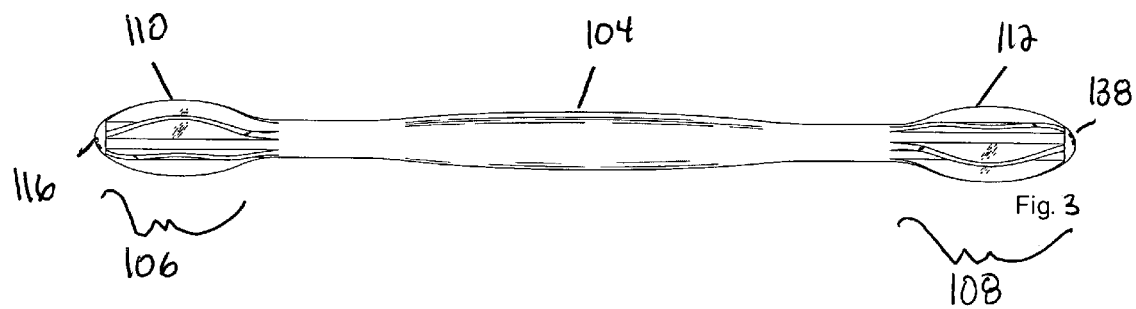
FIG. 3 is a side view of FIG. 1
Figure 4:
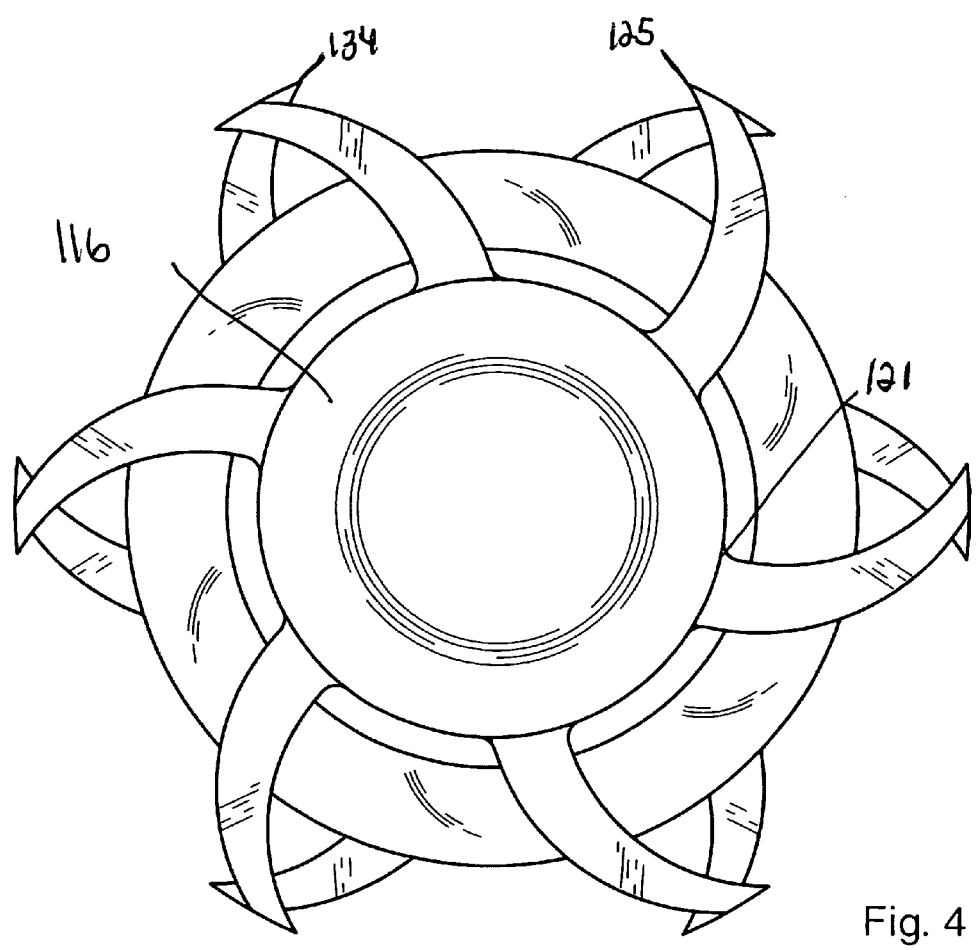
FIG. 4 is a cross-sectional view of FIG. 3, the section is taken perpendicular to the longitudinal axis of the FIG. 3.

Number Part Names 102 first embodiment
104 shaft
106 shaft first end
108 shaft second end
112 second plurality blades
114 shaft circular section
116 shaft first tip 118 longitudinal axis
120 first space
121 first arc radian
122 first curvature direction
124 blade section
125 first acute edge angle
126 second curvature direction
110 first plurality of blades
130 second arc radian
134 second acute edge angle
136 second space
138 shaft second tip First Embodiment FIG. 1 is a perspective view of the first embodiment of the current invention. FIGS. 2A through 2E are cross sections of FIG. 1, the sections indicated by lines 2A-2A, 2B-2B, 2C-2C, 2D-2D and 2E-2E respectively. FIG. 3 is a side view of FIG. 1. And FIG. 4 is a cross-sectional view of FIG. 3. Referring to FIG. 1, the first embodiment 102 has an elongated shaft 104. The elongated shaft 104 has blades 110 attached to the shaft first end 106 as shown, and a second plurality of blades 112 attached to the shaft second end 108. The cross section 2E-2E is taken along the longitudinal axis 118 of the elongated shaft 104 such that shaft is parallel to first plurality of blades 110 and the second plurality of blades 112. Cross section 2B has the same diameter of the shaft first end 106 as shown in FIG. 2A but has blade sections 124 that are smaller as compared to the blade sections 124 of FIG. 2A as indicated in FIG. 1.

Figure 2B:
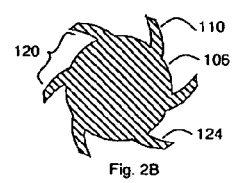
Figure 2C:
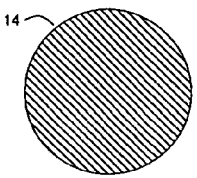

Each of the blades 110 has a curved shape as shown in FIGS. 2A and 2B. The first curvature direction 122 of each of the blades 110 is concave counterclockwise. The cross section in FIGS. 2A and 2B lies perpendicular to the longitudinal axis 118 of the elongated shaft 104. As indicated in FIG. 2A, the first curvature direction 122 of each of the blades occur in the same direction. The blades 110 are uniformly radially spaced on the about the longitudinal axis of the shaft 106 as indicated in FIG. 2A. The first plurality blades 110 curved from the base of the shaft 106 as shown in FIG. 4 having a first arc radian 121 that ranges from 20 degrees to 50 degrees. As best seen in FIG. 4 the first plurality of blades 110 are acute and first concave having a first acute edge angle 125 ranging from 3 to 7 degrees.

Figure 2D:
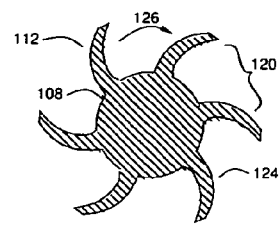
Figure 2E:
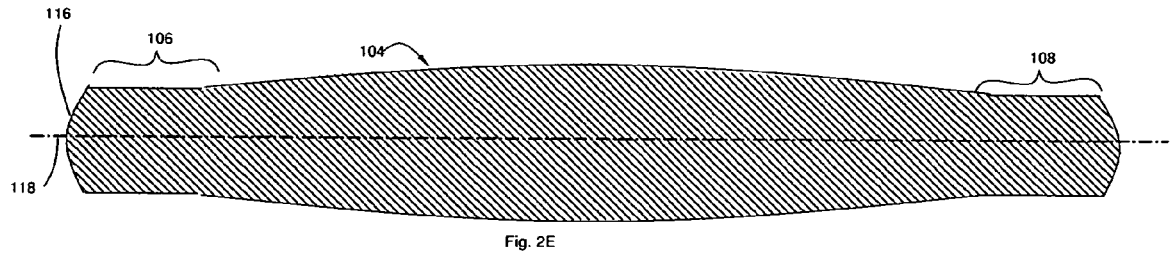
FIG. 2E is a section view of the shaft taken along the longitudinal axis

Referring to FIGS. 1, 2D and 2E, the second plurality of blades 112 are attached to the elongated shaft 104 at shaft second end 108. The second plurality blades 112 are each curved in the opposite direction of the first plurality of blades 110, i.e. second plurality of blades 112 are curved in the second curvature direction 126 which is convex clockwise. This is also indicated in FIGS. 2A and 2D since FIG. 2D is the mirror image of FIG. 2A. Referring to FIGS. 2A and 2B, the first space 120 between adjacent blades are designed to capture earwax and debris. Referring to FIG. 2D the second space 136 between adjacent blades are designed to capture earwax and debris. The blades are uniformly radially spaced 120 on the about the longitudinal axis of the shaft 108 as indicated in FIG. 2D. The second plurality blades 112 curved from the base of the shaft 108 as shown in FIG. 2D at a second arc radian 130 that ranges from 20 degrees 50 degrees. As best seen in FIG. 4 the second plurality of blades 112 are acute and second convex having a second acute edge angle 134 ranging from 3 to 7 degrees.

Referring to FIGS. 1 and 2E, the elongated shaft 104 is dually tapered, and has a shaft circular section 114. The shaft circular section 114 is shown taken at the longitudinal midpoint of the elongated shaft 104. As shown in FIGS. 1, 2A, 2B and 2E, the shaft is dually tapered as the distance from the shaft circular section 114 is increased, with the shaft first end 106 and shaft second end 108 ending the taper by having a regular cylindrical shape as shown in FIG. 2E. The shaft first end 106 as shown in FIG. 1, FIG. 3 and FIG. 4. As seen in FIG. 1, FIG. 3 the sections 2A and 2B the device has a bevel shape at the shaft first end 106 that tapers from the shaft first tip 116 to the midpoint of the blades 110. Referring to FIG. 3, the shaft second end 108 as shown in FIG. 3 the device has a bevel shape at the shaft second end 108 that tapers from the shaft second tip 138 to the midpoint of the blades 112. The shaft first tip 116 located at the shaft first end 106 is domed shaped adapted to protect the ear canal from sharp edges. The shaft second tip 138 located at the shaft second end 108 is domed shaped adapted to protect the ear canal from sharp edges.

The dimensions of the device is determined so that it fits comfortably inside the ear canal. In the first embodiment, the shaft tip 116 is approximately 3 mm (about 0.1181 inch), the length of the device is approximately 15 mm (0.5906 inch) and the diameter of the shaft circular section 114 is approximately 6 mm (0.2362 inch).

The first embodiment 102 is made from a single solid piece of polypropylene. Due to the shape of the curved blades, the first embodiment may be best made by 3-D printing or injection mold manufacturing. Injection mold manufacturing is the preferred way for manufacturing commercial products at the time of the filing this application.

Other Embodiments

Other embodiments are consistent with the teachings of this invention. The first embodiment has two sets of blades; an alternate embodiment may only have one set of blades, with the other set of blades replaced by a handle. In another alternate embodiment, the second plurality of blades 112 may be sized differently than the first plurality of blades 110, therefore providing a dual sizing capability. Hence this alternate embodiment may be used to clean the ear canals of an infant, child and adult, depending on the design.

In still another alternate embodiment, the first plurality of blades 110 and the second plurality of blades 112 may have the same dimensions, but the curvature of the two sets of blades may be in the same direction; i.e. FIG. 3D would be replaced by a copy of FIG. 3A. In a device constructed following this embodiment, the user can use the device when one end is inserted in the ear rotating the device in a clockwise direction, and then by inserting the device with the other end in the ear canal, the user can rotate the device in a counterclockwise direction.

Still other embodiments are consistent with the teachings of this invention. The number of blades may be from 1 to 20. The device may be made from materials other than plastic; e.g. it could be made of metal, wood, paper, or other materials.

In other alternate embodiments, the device may be manufactured using silicone, thermoplastic or other materials having a rigid or semi-rigid property.

What is claimed:

1. A device for inserting into an ear canal that rotates inside said ear canal and scrapes an optimal amount of earwax and debris from said ear canal without injuring said ear canal and ear drum, said device comprising:
   an elongated shaft having a first end and a second end and a longitudinal axis;
   a first plurality of blades attached to said first end being uniformly radially spaced on said first end about the longitudinal axis, the first plurality of blades being connected to a shaft parallel to the longitudinal axis, said first plurality of blades connected to said shaft parallel to the longitudinal axis, each adjacent pair of said first plurality of blades having a first space that is adapted to collect and store earwax and debris: said first plurality of blades are adapted to cut and scrape an optimal amount of earwax and debris from the surface of the ear canal;

wherein said first plurality of blades have a first curvature direction being concave clockwise from a base of said shaft parallel to the longitudinal axis with a first arc radian from 20 degrees to 50 degrees;

wherein said first plurality of blades each having a first concave and having a first acute edge angle ranging from 3 to 7 degrees adapted to cut and scrape said optimal amount of earwax and debris from the surface of the ear canal at a first angle ranging up to 45 degrees adapted to require less rotational force when rotated inside the ear canal;

a second plurality of blades attached to said second end being uniformly radially spaced on said second end about the longitudinal axis, the second plurality of blades being connected to the shaft parallel to the longitudinal axis, said second plurality of blades connected to said shaft parallel to the longitudinal axis, each adjacent pair of said second plurality of blades having a second space that is adapted to collect and store earwax and debris, said second plurality of blades are adapted to cut and scrape an optimal amount of earwax and debris from the surface of the ear canal;

wherein said second plurality of blades having a second curvature direction being convex clockwise from the base of the shaft parallel to the longitudinal axis with a second arc radian from 20 to 50 degrees; and wherein said second plurality of blades having edges that are second convex and having a second acute edge angles ranging from 3 degrees and 7 degrees adapted to cut and scrape said optimal amount of earwax and debris from the surface of the ear canal at a second angle ranging up to 45 degrees adapted to require less rotational force when rotated inside the ear canal.

2. The device in accordance with claim 1: wherein said device further comprises a tip at said shaft parallel to the longitudinal axis first end, said tip shaped like a dome, said tip adapted to protect said ear canal when said device is inserted and rotated in said ear canal.

3. The device in accordance with claim 1:
wherein said elongated shaft having a circular section of the device which is adapted to be grasped and rotated.

4. The device in accordance with claim 3:
wherein said device further comprises a tip at the second end of said shaft parallel to the longitudinal axis, wherein said tip shaped like a dome and adapted to protect said ear canal when said device is inserted and rotated in said ear canal.

5. The device in accordance with claim 3 further comprising:
said first plurality of blades having a bevel shape at the shaft first end that tapers from a first shaft tip to a midpoint of the first plurality of blades for minimizing the amount of earwax and debris being pushed inside ear canal upon insertion and adapted to reach earwax and debris located deeper inside the ear canal.

6. The device in accordance with claim 3 further comprising:
said second plurality of blades having a bevel shape at the shaft second end that tapers from a second shaft tip to a midpoint of the second plurality of blades for minimizing the amount of earwax and debris being pushed inside ear canal upon insertion and adapted to reach earwax and debris located deeper inside the ear canal.

7. The device in accordance with claim 1: wherein said device is injection molded from plastic comprising one of polypropylene and polyethylene, or a combination thereof.

* * * * *